United States Patent [19]

Van Herrtum et al.

[11] Patent Number: 4,687,509
[45] Date of Patent: Aug. 18, 1987

[54] N,N,N-TRIBUTYL-(3-HYDROXYBENZYL-)AMMONIUM SALTS AND A METHOD FOR INCREASING YIELD OF SOYBEANS

[75] Inventors: John C. Van Herrtum, Concord; Theodore W. Holmsen, Clayton, both of Calif.

[73] Assignee: The Dow Chemical Company, Midland, Mich.

[21] Appl. No.: 864,678

[22] Filed: May 19, 1986

[51] Int. Cl.$^4$ .................................................. A01N 33/12
[52] U.S. Cl. ........................................................ 71/121
[58] Field of Search ................... 71/121; 564/285, 287

[56] References Cited

U.S. PATENT DOCUMENTS

| | | | |
|---|---|---|---|
| 2,647,924 | 8/1953 | Aeschlimann et al. | 564/287 |
| 3,399,226 | 8/1968 | Saari | 564/287 |
| 3,506,433 | 4/1970 | Abramitis et al. | 71/121 |
| 3,809,646 | 5/1974 | Spence | 564/287 |
| 4,040,813 | 8/1977 | Newhall | 71/121 |
| 4,299,618 | 11/1981 | Downing et al. | 71/121 |
| 4,343,647 | 8/1982 | Dunbar et al. | 71/121 |
| 4,488,901 | 12/1984 | Farkas et al. | 71/121 |

FOREIGN PATENT DOCUMENTS 41-6597  4/1966  Japan ..................................... 71/121

OTHER PUBLICATIONS

Epstein et al., J.A.C.S., vol. 86, pp. 3075–3084 (1964).
Teitel'baum et al., Chem. Abst., vol. 99, #87397a (1983).

Primary Examiner—James H. Reamer
Attorney, Agent, or Firm—S. Preston Jones; Ronald G. Brookens

[57] ABSTRACT

The yield of soybeans can be increased by treating the plants during the period from full bloom to the beginning of the seed filling period with N,N,N-tributyl-(3-hydroxybenzyl)ammonium salts.

4 Claims, No Drawings

N,N,N-TRIBUTYL-(3-HYDROXYBENZYL)AMMONIUM SALTS AND A METHOD FOR INCREASING YIELD OF SOYBEANS

BACKGROUND OF THE INVENTION

An active area of agricultural research is devoted to the production of more productive plant life, particularly that plant life associated with food sources for man. In this research much effort has been expended in developing means for the regulation of the growth pattern of plant life, particularly as evidenced by the retardation of growth, the enhancement of growth and the enhancement of maturation.

These objectives have been accomplished, in part, by the development and distribution of various chemical agents which alter or modify the growth characteristics of plants.

DESCRIPTION OF THE PRIOR ART

In U.S. Pat. No. 3,923,495, (carboxybenzyl)trialkylammonium salts are taught as growth regulators of various plants, including soybeans. The treatment of soybean plants at early flowering, i.e., 6 weeks after planting, is taught. It is indicated that no significant yield increase was observed. Because of the inability of these compounds to give a significant yield increase, they have been held as not being commercially meaningful.

A method for increasing soybean yield is taught in U.S. Pat. No. 4,299,618 employing trialkyl-2,4-dichlorobenzylammonium chlorides. The material is applied at the 5–8 trifoliate leaf stage for Northern indeterminate varieties and at 10–11 trifoliate leaf stage for Southern determinate varieties. While yield increases are shown, these increases are not consistent and vary substantially. Such inconsistency is not commercially acceptable.

In U.S. Pat. No. 4,343,647 certain substituted benzyltrialkylammonium salts are described and their use as plant growth regulatory control agent. These compounds are described as active in causing a reduction or stunting of the linear growth of various plants such as soybeans, silver maple, eucalyptus, black oak, Arizona cypress and sweet gum.

SUMMARY OF THE INVENTION

The present invention is directed to a compound corresponding to the formula

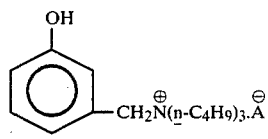

wherein

A represents a non-phytotoxic anion. The present invention is also directed to the preparation of the compound, compositions containing the compound and to a method for increasing the yield of soybeans which comprises treating the soybean plants during the mid-bloom term.

The specific anion of the compounds of the present invention is not critical. The anion can be any of the anions conventionally employed in plant growth regulators. The only limitation upon the anion chosen is that it be non-phytotoxic to the plants being treated. Representative anions include $Cl^{(-)}$, $Br^{(-)}$, $I^{(-)}$, $SCN^{(-)}$, $CH_3CO_2^{(-)}$, $C_2H_5CO_2^{(-)}$, $\phi SO_3^{(-)}$, $\phi CO_2^{(-)}$, $Cl-\phi-O^{(-)}$, $C_3H_7CO_2^{(-)}$, $SO_4^{(=)}$, $PO_4^{(\equiv)}$, $NO_3^{(-)}$, $ClO_3^{(-)}$ and $N_3^{(-)}$, among others.

The compound of the present invention are usually prepared in a multistep procedure which can be characterized as follows:

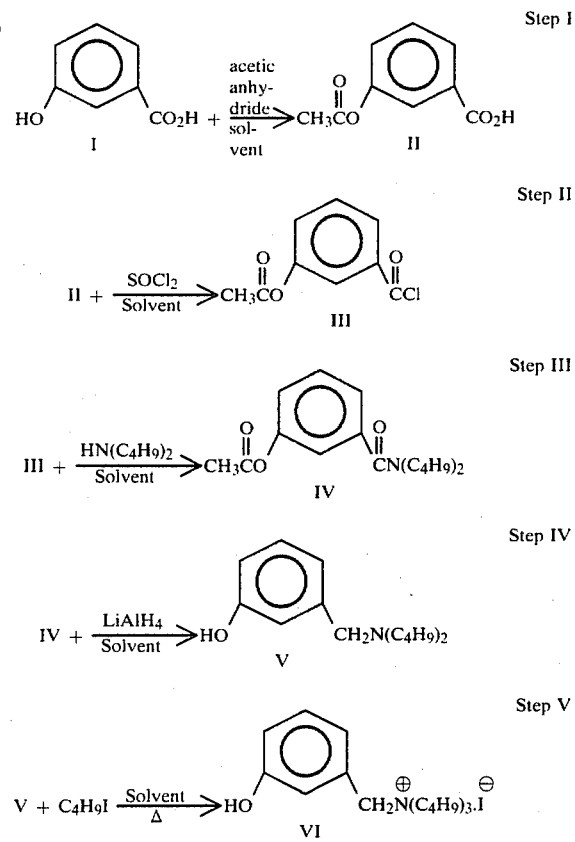

While the above preparative procedures have been described wherein the product is in the form of the iodide salt, other salts can be prepared employing conventional procedures.

Such additional salts are prepared by treating the iodide product at room temperature in water with the alkali or alkaline earth salt of the organic or inorganic acid from which the desired anion is derived. This salt is of the formula $$M^{\oplus}Z^{\ominus}$$

wherein M represents the alkali metals such as sodium, potassium, lithium, cesium or rubidium and the alkaline earth metals such as calcium, barium or strontium and Z is as hereinabove set forth. These additional salts can also be prepared by passing the product salt through an ion exchange column charged with the appropriate anion.

DESCRIPTION OF SOME PREFERRED EMBODIMENTS

The following examples illustrate the present invention and the manner by which it can be practical but, as such, should not be construed as limitations upon the overall scope of the same.

EXAMPLE I

N,N,N-tributyl-(3-hydroxybenzyl)ammonium iodide

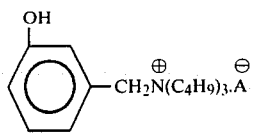

Step A

A mixture was prepared of 81 grams (g) (0.58 mole (m)) of m-hydroxybenzoic acid, in 100 milliliters (ml) of acetic anhydride. The mixture was heated and refluxed for 5 hours. Toluene was added and the mixture filtered. The filtrate was evaporated and the filter cake was washed very well with hexane and dried. The 3-acetoxybenzoic acid product was obtained, as a white powder, in a yield of 112.7 g.

Step B

The product prepared above was mixed with 150 ml of thionyl chloride, and 1 ml of dimethylformamide and heated to reflux for 1 hour. The thionyl chloride was evaporated off. The acid chloride product distilled at 90° C.–95° C. at 0.02 mm and was obtained in a yield of 104.7 g as a colorless oil.

Step C

The acid chloride product, prepared as above (0.527 mole), was mixed with 400 ml of methylene chloride. To this mixture was added dropwise 177 ml of dibutylamine while maintaining the temperature below 25° C. After the completion of the reaction, the reaction mixture was washed with dilute sodium hydroxide and the methylene chloride layer was evaporated off. The residual material was dissolved in hexane and washed with water and dried and the solvent evaporated off. The 3-acetoxy-N,N-dibutylbenzamide product distilled at 130° C.–135° C. at 0.01 mm and, was recovered, as a pale yellow oil in a yield of 145.9 g.

Step D

A mixture of 33.0 g (0.133 m) of 3-acetoxy-N,N-dibutylbenzamide in 400 ml of ether was slowly added over one half hour to a suspension of 5.0 (0.133 m) grams of lithium aluminum hydride (LAH) in 300 ml of ether. The mixture was heated to reflux for 2 hours. The mixture was slowly treated with 5.0 ml of water, 5.0 ml of 15% sodium hydroxide and 15.0 ml of water. Magnesium sulfate was added and stirred well. The mixture was filtered and washed well with ether. The solvent was evaporated off leaving the 3-hydroxy N,N-dibutylbenzylamine product in a yield of 23.3 g. The product was a yellow oil with a refractive index of n(25/D)=1.5172.

Step E

A mixture was prepared containing 10 g (0.042 m) of 3-hydroxy N,N-dibutylbenzylamine, 15 g (0.082 m) of butyliodide and 25 ml of acetonitrile. The mixture was heated to reflux overnight. The completion of the reaction was determined by high pressure liquid chromatography. After completion, the solvent was removed and the residue triturated with ether, filtered and dried. The desired N,N,N-tributyl-(3-hydroxybenzyl)ammonium iodide product was recovered as a white powder in a yield of 15.7 g. The product melted at 128° C.–130° C. and its elemental analysis is as follows:

| | Analysis: | | |
|---|---|---|---|
| | % C | % H | % N |
| Calc. for $C_{19}H_{34}INO$: | 54.41 | 8.17 | 3.34 |
| Found: | 53.01 | 8.13 | 3.31 |

Infrared and Nuclear Magnetic Resonance (NMR) were employed to confirm the obtainment of the products of each of the above steps.

The exposure of viable soybean plants to the action of an effective amount of the active compound employed in the present invention during the mid-bloom term during the middle of (R1–R2 as explained hereinbelow) is essential and critical for the practice of the present invention. While the active compound can be applied during other growth stages of the plant, yield increases, if they occur, will not be as consistent as when treatment occurs during the specific growth stages as set forth in the present invention.

In the report "Stages of Soybean Development" Fehr et al., Special Report 80, March 1977, Cooperative Extension Service, Agriculture and Home Economics Experiment Station, Iowa State University, the authors discuss the growth of soybean plants and sets forth a table describing the vegetative and reproductive stages.

Vegetative stages are described from the time the plant emerges from the soil. After the cotyledon (VC) stage, nodes are counted beginning with the unifoliolate nodes. The unifoliolate nodes are technically two separate nodes, but they are counted as one because they occur at the same position and time on the main stem.

Only nodes on the main stem are counted. Nodes on branches should not be considered. If the main stem is broken or cut off, new branches that develop should not be used to determine vegetative stages. Development of the new growth will be behind that of a main stem that has not been cut off.

Each stage description (table 1) is given a vegetative stage (V) designation and an abbreviated title to facilitate communication. Vegetative stage numbers are determined by counting the number of nodes on the main stem, beginning with the unifoliolate nodes, that have or have had a fully developed leaf.

TABLE 1

| Stage No. | Abbreviated Stage Title | Description |
|---|---|---|
| VE | Emergence | Cotyledons above the soil surface |
| VC | Cotyledon | Unifoliolate leaves unrolled sufficiently so the leaf edges are not touching |
| V1 | First-node | Fully developed leaves at unifoliolate nodes |
| V2 | Second-node | Fully developed trifoliolate leaf at the node above the unifoliolate nodes |
| V3 | Third-node | Three nodes on the main stem with fully developed leaves beginning with the unifoliolate nodes |
| V(n) | nth-node | n number of nodes on the main stem with fully developed leaves beginning with the unifoliolate nodes. n can be any number beginning with 1 for V1, |

TABLE 1-continued

Description of Vegetative Stages

| Stage No. | Abbreviated Stage Title | Description |
|---|---|---|
| | | first-node stage |

Reproductive stages are based on flowering, pod development, seed development, and plant maturation. Each stage description is given a reproductive stage (R) number and an abbreviated title (table 2).

The main stem must be used for determining reproductive stages. When the main stem of a plant is broken or cut off, reproductive development on the new branches may be retarded.

Stages R1 and R2 (table 2) may occur simultaneously in determinate varieties because flowering begins at the upper nodes of the main stem. The two stages are approximately 3 days apart for indeterminate varieties, in which flowering begins in the lower portion of the main stem and progresses upward.

Pods reach nearly full size before the seed begins to develop rapidly. Pod measurements for R3 and R4 are made from the base of the calyx (leaf-like tissue at the bottom of the pod) to the tip of the pod. When pods are 2 cm (centimeters) long at R4, the pod cavity in which each seed will develop is outlined by a white membrane. At R6 the seed has enlarged enough to cover the entire membrane. The seed continues to get thicker after R6 until its full size is achieved.

As the soybean plant matures, leaf and pod yellowing generally occur simultaneously. In some circumstances, however, leaves may remain green after the pods have attained their mature pod color.

Soybean varieties differ in their mature pod color. The most common colors are brown and tan, but soybean lines are known that have black pods.

TABLE 2

Description of Reproductive Stages

| Stage No. | Abbreviated Stage Title | Description |
|---|---|---|
| R1 | Beginning bloom | One open flower at any node on the main stem. |
| R2 | Full bloom | Open flower at one of the two uppermost nodes on the main stem with a fully developed leaf. |
| R3 | Beginning pod | Pod 5 mm (3/16 inch) long at one of the four uppermost nodes on the main stem with a fully developed leaf. |
| R4 | Full pod | Pod 2 cm (¾ inch) long at one of the four uppermost nodes on the main stem with a fully developed leaf. |
| R5 | Beginning seed | Seed 3 mm (⅛ inch) long in a pod at one of the four uppermost nodes on the main stem with a fully developed leaf. |
| R6 | Full seed | Pod containing a green seed that fills the pod cavity at one of the four uppermost nodes on the main stem with a fully developed leaf. |
| R7 | Beginning maturity | One normal pod on the main stem that has reached its mature pod color. |
| R8 | Full maturity | Ninety-five percent of the pods that have reached their mature pod color. Five to ten days of drying weather are required after R8 before |

TABLE 2-continued

Description of Reproductive Stages

| Stage No. | Abbreviated Stage Title | Description |
|---|---|---|
| | | the soybeans have less than 15 percent moisture. |

The exact yield increasing dosage to be employed is dependent upon many factors such as climatic conditions such as temperature, wind and especially rainfall. In foliar treatments good yield increases are obtained when from 0.05 to 5 ounces per acre preferably 0.2 to 3 ounces per acre of the compound is applied.

The method of the present invention can be practiced by distributing the unmodified compound upon the surfaces of the aboveground portion of plants. However, the present method also embraces the similar employment of liquid or dust compositions containing the compound. In such usages, the compound can be modified with one or a plurality of additaments or adjuvants including water or other liquid carriers, surface active dispersing agents, and finely divided solids. Depending upon the concentration of the compound, such augmented compositions are adapted to be distributed upon the aboveground surfaces of plants, or to be employed as concentrates and subsequently diluted with additional inert carrier to produce the ultimate treating compositions. In compositions where the adjuvant or helper is a finely divided solid, a surface active agent or the combination of a surface active agent and a finely divided solid, and/or a liquid additament, the adjuvant and/or adjuvants cooperate with the compound so as to facilitate the invention and obtain an improved and outstanding result.

The exact concentration of the compound to be employed in the treating compositions is not critical and may vary considerably provided the required dosage of the compound is supplied upon the plant foliage. The concentration of the compound in liquid compositions employed to supply the desired dosage generally is from about 0.001 to 50 percent by weight although concentrations as low as 0.0001 percent and as high as 90 percent by weight are sometimes advantageously employed. In dusts, the concentration of active ingredient is from about 0.1 to 90 percent by weight and usually not in excess of about 20 percent. In both liquid and dust compositions to be employed as concentrates, the compound can be present in a concentration of from 5 to 98 percent by weight.

The quantity of treating composition to be applied can vary considerably provided that the required dosage of the compound or active ingredient is applied in a sufficient amount of the finished composition to cover adequately the vegetation to be treated; good coverage is obtained when using from 1 to 50 gallons of finished spray composition per acre. In the application of dusts to plant foliage, good results are obtained with from 10 to 1000 pounds of finished dust per acre, the only requirement being that the required active ingredient dosage be supplied in sufficient dust to achieve good coverage of the foliage.

Liquid compositions containing the desired amount of active ingredient can be prepared by dispersing the compound in water or in organic liquid, with or without the aid of a suitable surface active dispersing agent such as an ionic or non-ionic emulsifying agent. Suitable organic liquid carriers include the agricultural spray oils and the petroleum distillates such as diesel fuel, kerosene, fuel oil, and naphthas. The organic liquid compositions can contain a small amount of water as a solvent for the active ingredient. In such compositions, the carrier comprises an emulsion, namely, a mixture of water, emulsifying agent, and organic liquid. In the liquid compositions, the choice of dispersing and emulsifying agent and the amount thereof employed is dictated by the nature of the composition and by the ability of the agent to facilitate the dispersion of the compound in the carrier to produce the desired composition or to facilitate the wetting of surfaces upon which the compositions are applied. Dispersing and emulsifying agents which can be employed in the compositions include the condensation products of alkylene oxides with phenols and organic acids, alkyl aryl sulfonates, polyoxyalkylene derivatives of sorbitan esters, complex ether alcohols, mahogany soaps and the like.

In the preparation of dust compositions, the active ingredient is dispersed in and on a finely divided solid such as clay, talc, chalk, gypsum, sugar, salt, bicarbonate, fertilizer and the like. In such operations, the finely divided carrier is mechanically mixed or ground with the compounds. Similarly, dust compositions containing the compound can be prepared from various of the solid surface active dispersing agents such as bentonite, fuller's earth, attapulgite, and other clays. Depending upon the proportion of ingredients, these dust compositions can be employed as concentrates and subsequently diluted with additional solid surface active dispersing agent or with chalk, talc or gypsum, sugar, salt, fertilizer, and the like to obtain the desired amount of active ingredient in a composition adapted to be employed for the modification of the growth of plants. Also such dust compositions can be dispersed in water with or without the aid of a dispersing agent to form spray mixtures.

The expression "surface active dispersing agent" as herein employed is intended to include all agents which are capable of acting at the interfacial surface as the dispersion medium. Thus, the term is inclusive of the solid emulsifying agents such as finely divided aluminum hydroxide, finely divided bentonite, fuller's earth, attapulgite, or other clays, as well as the ionic and non-ionic wetting and emulsifying agents such as the alkaline earth metal caseinates, alkyl aryl sulfonates, sulfonated oils, complex organic ester derivatives, complex ether alcohols, or the like.

The finely divided inert solid or carrier as herein described refers to materials which are incapable of facilitating dispersion, but which serve as a distribution medium for the active compounds. They include finely divided materials such as chalk, talc, gypsum, sugar, salt, bicarbonate, or fertilizers.

The following examples further illustrate the present invention.

EXAMPLE II

Tests were conducted to determine the effectiveness of tri-n-butyl-(3-hydroxybenzyl)ammonium iodide in increasing the yield of soybeans.

Soybean seeds of the variety Williams 79 were planted in 30 inch rows in 10×25 foot plats, with 6 replications. About seven weeks after planting, the plants were in mid-bloom (between Stages R1 and R2) and the plants were sprayed with various dilutions of aqueous solutions of tri-n-butyl-(3-hydroxybenzyl)ammonium iodide at the rate of 15 gallons of total solution for each dilution rate. These solutions were prepared by dissolving a predetermined amount of the compound in a predetermined amount of water containing 0.1 percent of a wetting agent. Like plants treated only with water and wetting agent were maintained as controls.

The plants were allowed to mature and one square meter ($m^2$) plots were harvested about 22 weeks after planting. The dosage of the treatments and the results obtained were as follows:

| Test Chemical | Dosage in Ounces per Acre | Yields as a Percent of Control | | |
| --- | --- | --- | --- | --- |
| | | Height of Plants at Maturity | Number of Pods/$m^2$ | Seed Weight /$m^2$ |
| tri-n-butyl-(3-hydroxy-benzyl)ammonium iodide | 0.35 | 87 | 110 | 113 |
| | 5.0 | 78 | 115 | 111 |

What is claimed is:

1. A composition useful for treating soybean plants to increase the yield of soybeans which contains an inert carrier in admixture with an active compound corresponding to the formula

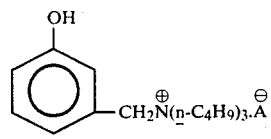

wherein A represents a non-phytotoxic anion.

2. The composition as defined in claim 1 wherein the active compound is N,N,N-tributyl-(3-hydroxybenzyl)ammonium iodode.

3. A method for increasing the yield of soybeans which comprises treating said soybean plants during the mid-bloom period with a yield increasing amount of a composition which contains an inert carrier in admixture with an active compound corresponding to the formula

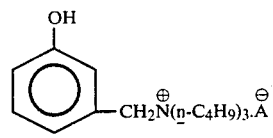

wherein A represents a non-phytotoxic anion.

4. The method as defined in claim 3 wherein the active compound is N,N,N-tributyl-(3-hydroxybenzyl)ammonium iodide.

* * * * *